(12) United States Patent
Mao et al.

(10) Patent No.: US 12,274,421 B2
(45) Date of Patent: *Apr. 15, 2025

(54) DEVICE FOR ANTI-FOG ENDOSCOPE SYSTEM

(71) Applicant: Novelbeam Technology Inc., San Jose, CA (US)

(72) Inventors: Rongzhuang Mao, Shandong (CN); Changming Gu, Shandong (CN); Mingzhi Li, Shandong (CN); James Zheng, Fremont, CA (US); Anmin Zheng, Fremont, CA (US); Daniel Cifelli, Fremont, CA (US)

(73) Assignee: Novelbeam Technology Inc., San Jose, CA (US)

( * ) Notice: Subject to any disclaimer, the term of this patent is extended or adjusted under 35 U.S.C. 154(b) by 198 days.

This patent is subject to a terminal disclaimer.

(21) Appl. No.: 17/162,181

(22) Filed: Jan. 29, 2021

(65) Prior Publication Data

US 2021/0251478 A1 Aug. 19, 2021

(30) Foreign Application Priority Data

Feb. 17, 2020 (CN) .......................... 202010095217.0

(51) Int. Cl.
*A61B 1/06* (2006.01)
*A61B 1/00* (2006.01)
(Continued)

(52) U.S. Cl.
CPC ........ *A61B 1/0646* (2013.01); *A61B 1/00078* (2013.01); *A61B 1/00096* (2013.01);
(Continued)

(58) Field of Classification Search
CPC .............. A61B 1/0646; A61B 1/00078; A61B 1/00121; A61B 1/00186; A61B 1/00188;
(Continued)

(56) References Cited

U.S. PATENT DOCUMENTS

| 4,788,441 A | 11/1988 | Laskowski |
| 6,063,024 A * | 5/2000 | Yamamoto ............. A61B 1/042 |
| | | 600/178 |

(Continued)

FOREIGN PATENT DOCUMENTS

| CN | 104545775 A | 4/2015 |
| CN | 103654701 B | 8/2016 |

(Continued)

OTHER PUBLICATIONS

PCT/US2021/018405 , "International Search Report and Written Opinion", Apr. 28, 2021, 12 pages.

(Continued)

*Primary Examiner* — Thong Q Nguyen
(74) *Attorney, Agent, or Firm* — Kilpatrick Townsend & Stockton LLP

(57) ABSTRACT

A device for maintaining an optical path of an optical imaging system free of fog includes an elongated member having a distal end and a proximal end, a near-infrared (NIR) light-absorbing optical window disposed at the distal end, and an optical system disposed along the optical path. The device also includes a coupling module coupled to the elongated member at the proximal end and configured to transmit near-infrared light to the NIR light-absorbing optical window along the optical path and receive a light beam from an area of interest along the optical path.

20 Claims, 13 Drawing Sheets

(51) Int. Cl.
    *A61B 1/018*     (2006.01)
    *A61B 1/04*     (2006.01)
    *A61B 1/05*     (2006.01)
    *A61B 1/12*     (2006.01)
    *G02B 5/20*     (2006.01)
    *G02B 13/14*     (2006.01)
    *G02B 27/00*     (2006.01)
    *G02B 27/14*     (2006.01)
    *G02B 27/30*     (2006.01)

(52) U.S. Cl.
    CPC ...... *A61B 1/00121* (2013.01); *A61B 1/00126* (2013.01); *A61B 1/00163* (2013.01); *A61B 1/00186* (2013.01); *A61B 1/00188* (2013.01); *A61B 1/018* (2013.01); *A61B 1/04* (2013.01); *A61B 1/05* (2013.01); *A61B 1/0638* (2013.01); *A61B 1/0661* (2013.01); *A61B 1/0684* (2013.01); *A61B 1/127* (2013.01); *G02B 5/208* (2013.01); *G02B 13/14* (2013.01); *G02B 27/0006* (2013.01); *G02B 27/141* (2013.01); *G02B 27/30* (2013.01)

(58) Field of Classification Search
    CPC ......... A61B 1/018; A61B 1/05; A61B 1/0638; A61B 1/0661; A61B 1/127; A61B 1/00096; A61B 1/002; A61B 1/042; A61B 1/0669; A61B 1/07; A61B 1/00163; A61B 1/3132; G02B 5/208; G02B 13/14; G02B 27/0006; G02B 27/141; G02B 27/30; G02B 23/2446; G02B 23/2469; G02B 27/1006
    USPC ................ 359/350–361, 368–398, 577–598, 359/885–892, 512
    See application file for complete search history.

(56) References Cited

U.S. PATENT DOCUMENTS

| | | | |
|---|---|---|---|
| 6,503,196 B1 | 1/2003 | Kehr et al. | |
| 6,911,177 B2 | 6/2005 | Deal | |
| 7,662,095 B2* | 2/2010 | Irion | A61B 1/0669 600/181 |
| 8,105,532 B2 | 1/2012 | Harmon et al. | |
| 8,226,887 B2 | 7/2012 | Harmon et al. | |
| 8,779,391 B2 | 7/2014 | Flaherty et al. | |
| 8,974,924 B2* | 3/2015 | Weber | H04M 1/0202 428/688 |
| 10,092,669 B2 | 10/2018 | Marshall | |
| 10,597,156 B2 | 3/2020 | Viel | |
| 10,603,394 B2 | 3/2020 | Farren et al. | |
| 10,639,387 B2 | 5/2020 | Bonutti et al. | |
| 11,547,288 B2* | 1/2023 | Mao | A61B 1/00188 |
| 2005/0277810 A1 | 12/2005 | Irion | |
| 2009/0201577 A1* | 8/2009 | LaPlante | G01N 21/6458 313/501 |
| 2014/0200406 A1 | 7/2014 | Bennett et al. | |
| 2015/0085095 A1 | 3/2015 | Tesar | |
| 2015/0260889 A1 | 9/2015 | Shiono et al. | |
| 2017/0293134 A1* | 10/2017 | Otterstrom | A61B 1/0638 |
| 2018/0360298 A1* | 12/2018 | Khettal | A61B 1/00179 |
| 2019/0290113 A1* | 9/2019 | Uchimura | G02B 7/008 |

FOREIGN PATENT DOCUMENTS

| | | | |
|---|---|---|---|
| CN | 109965830 A | | 7/2019 |
| JP | 5781801 U | | 5/1982 |
| JP | 9-294706 | * | 11/1997 |
| JP | 11332821 A | | 12/1999 |
| JP | 2003334157 A | | 11/2003 |
| JP | 2016202627 A | | 12/2016 |
| JP | 2019165855 A | | 10/2019 |
| KR | 101798141 B1 | | 11/2017 |
| WO | 2004098398 A2 | | 11/2004 |
| WO | 2014088063 A1 | | 6/2014 |

OTHER PUBLICATIONS

Application No. PCT/US2021/018405, International Preliminary Report on Patentability, Mailed on Sep. 1, 2022, 10 pages.
Application No. EP21756827.8, Extended European Search Report, Mailed on Feb. 8, 2024, 8 pages.
Japanese Application No. 2022-549368, Office Action mailed on Feb. 3, 2025, 12 pages (5 pages of Original Document and 7 pages of English Translation).
Application No. CN202010095217.0, Notice of Decision to Grant, Mailed On Mar. 29, 2022, 2 pages, Translation begins on p. 2.
Application No. CN202010095217.0, Office Action, Mailed On Nov. 3, 2021, 14 pages, Translation begins on p. 8.

* cited by examiner

DEVICE FOR ANTI-FOG ENDOSCOPE SYSTEM

CROSS-REFERENCES TO RELATED APPLICATIONS

This application claims priority to Chinese patent application No. 202010095217.0, filed on Feb. 17, 2020, the contents of which are hereby incorporated by reference in their entirety for all purposes.

BACKGROUND OF THE INVENTION

When using rigid endoscopes for minimally invasive surgeries, especially for laparoscopic (abdominal) surgery, the temperature difference between the endoscope and the inside of the body, along with the humid conditions inside, causes fog to build up on the endoscope's protective window. The fogged up window blurs the images produced and has been a problem in the industry for decades. To the present, there has not been a satisfactory technical solution.

Thus, there is a need for a novel device and method that can prevent the fogging up of endoscope systems and/or mechanical or medical instruments.

SUMMARY OF THE INVENTION

The present disclosure generally relates to endoscopes, and more particularly, to an anti-fog optical imaging system for endoscopes and other minimally invasive medical devices.

An objective of the present disclosure is to provide novel solutions to defog endoscopes and mechanical medical instruments that can avoid the problems of image quality degradation that are associated with conventional techniques.

In one embodiment, a device for maintaining an optical path of an optical imaging system free of fog includes an elongated member having a distal end and a proximal end, a near-infrared (NIR) light-absorbing optical window disposed at the distal end, and an optical system disposed along the optical path. The device also includes a coupling module coupled to the elongated member at the proximal end and configured to transmit near-infrared light to the NIR light-absorbing optical window along the optical path and receive a light beam having wavelengths in a first range along the optical path.

One embodiment of the present disclosure provides a method of operating a fog-free optical imaging system having an elongated member comprising a distal end and a proximal end, a near-infrared (NIR) light-absorbing optical window disposed at the distal end, and an optical system along an optical path. The method includes coupling a coupling module to the elongated member at the proximal end, wherein the coupling module comprises a light source emitting NIR light, activating the light source to transmit the NIR light to the NIR light-absorbing optical window along the optical path for an illumination time period, and receiving a visible light beam reflected from an area of interest along the optical path.

Embodiments of the present disclosure provide improved safety, image quality, and convenience for a user or operator by preventing fog built up in an optical imaging system. Embodiments of the present disclosure also reduce the probability of missing tissue disease or the extent (boundary) of the tissue disease, the probability of misinterpreting good from bad tissue, and the probability of error and needing to operate a second time. Other advantages and benefits of the present disclosure include reduction of operation procedure time and operation room (OR) personnel fatigue because OR personnel are not constantly trying to get a clear image.

These and other embodiments of the present disclosure along with many of its advantages and features are described in more detail in conjunction with the text below and attached figures.

DETAILED DESCRIPTION OF THE INVENTION

The present disclosure generally relates to endoscopes and medical instruments. More specifically, the present disclosure relates to an anti-fog device that is operable to reduce or eliminate fogging in endoscopes and other minimally invasive medical devices. The anti-fog device can work with any type of viewing apparatus or illumination apparatus to maintain a fog-free optical image.

It is noted that, although embodiments of the present disclosure describe an anti-fog device that operates in endoscope systems, the present invention is not limited thereto. For example, the anti-fog device can be used in any viewing apparatus or illuminating apparatus that may face the problem of moisture built-up on a surface of an optical window. Examples of these viewing or illuminating apparatuses include eye glasses, safety goggles, and surgical protective head gears. Other examples may include flexible medical endoscopes and flexible fiberscopes or borescopes, telescopes (astronomy), rifle scope sights, binoculars, camera lenses (e.g., cell phone camera lenses), etc.

One solution for removing the fog resulting from the temperature difference between the endoscope and the inside of the body uses electrical current to heat up the endoscope's protective window. However, this solution can lead to inadvertent tissue damage and has, thus, not been widely used.

Other solutions include a light source for shining light with a specific wavelength on the endoscope's window to safely heat it up for reducing the fog build-up. For example, the Chinese patent application number 201210324982.0 discloses a device and method for defogging endoscopes using light to increase temperature and reduce fogging. However, because of reflections of stray light off of the front window, the image quality is degraded, thereby decreasing the product's marketability.

Figure 1A:
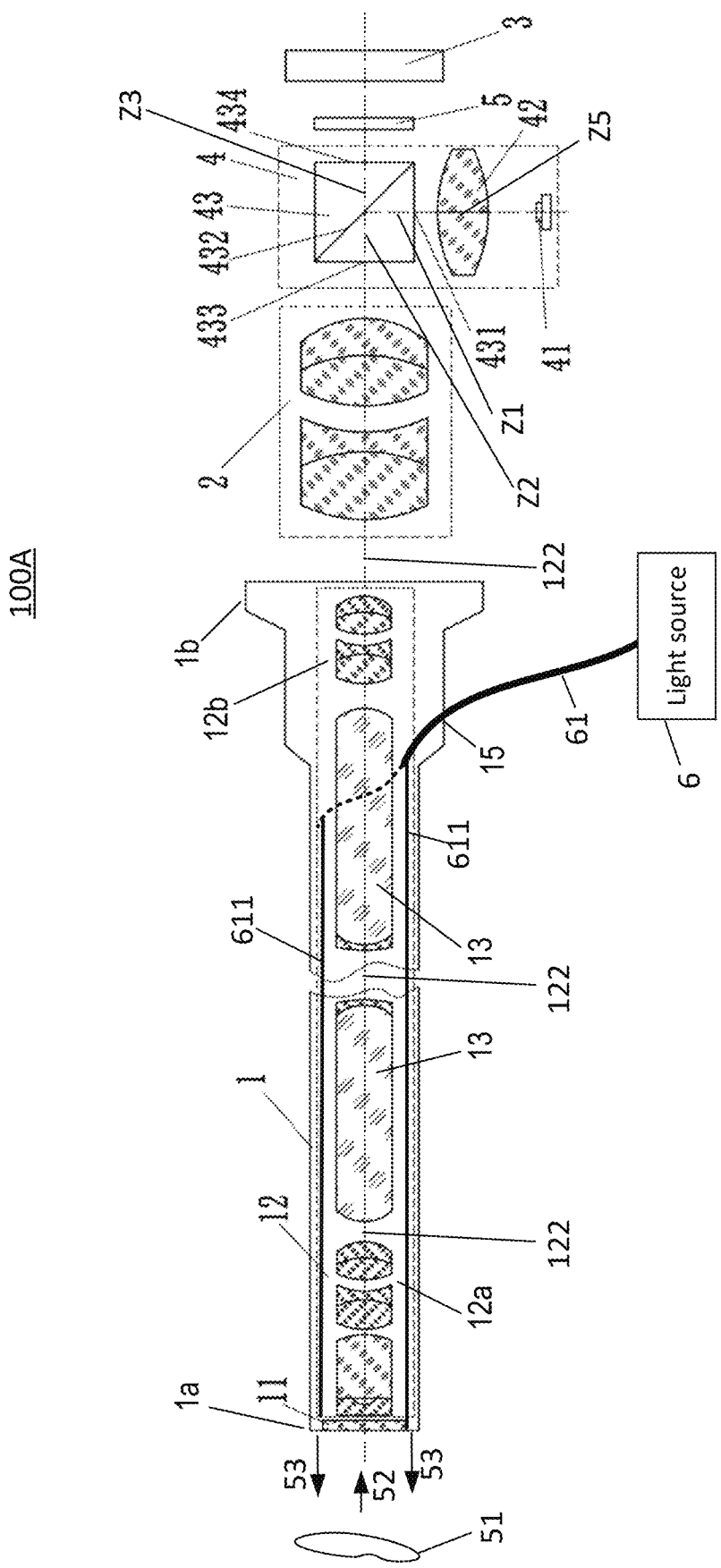
FIG. 1A is a cross-sectional view of an anti-fog device for defogging an endoscope or a medical instrument according to an embodiment of the present disclosure.

FIG. 1A is a cross-sectional view of an anti-fog device 100A for defogging an endoscope or a medical instrument according to an embodiment of the present disclosure. The anti-fog device (also referred to as "device" herein) 100A includes an elongated member 1 having a distal end 1a and a proximal end 1b, an optical adapter module 2, and an image sensor 3. Elongated member 1 may include a (rigid) endoscope or laparoscope system or a part of an endoscope or laparoscope system and contains a front optical window 11 and an optical system 12. Optical system 12 and optical adapter module 2 each have an imaging wavelength range of $\lambda 1$ to $\lambda 2$ ($\lambda 2 > \lambda 1$). In some embodiments, anti-fog device 100A may include a visible light only imaging system. In this case, the imaging wavelength range of $\lambda 1$ to $\lambda 2$ may be in the range of 400 nm to 700 nm or a subset of the 400 nm to 700 nm, and near infrared (NIR) anti-fog light can be longer than 700 nm because no NIR imaging, such as use of indocyanine green (ICG), is taking place as long as front optical window (NIR absorption window) 11 is properly matched. In other embodiments, anti-fog device 100A may include a visible light and near infrared (NIR) imaging system. In this case, NIR anti-fog light should have wavelengths longer than the fluorescence wavelength range for ICG (e.g., >900 nm), i.e., optical system 12 and optical adapter module 2 each may include an additional fluorescence emission based infrared region 23 around 814 nm with a 40 nm bandwidth for an NIR excitation light having a wavelength range of about 780 nm to about 800 nm. Optical system 12 and optical adapter module 2 are disposed along a common optical path 122. Optical system 12 may include a plurality of optical lens elements and one or more optical guides 13. In one embodiment, the plurality of optical lens elements may include a first set of optical lens elements 12a disposed in the vicinity of the distal end 1a and a second set of optical lens elements 12b disposed in the vicinity of the proximal end 1b of elongated member 1. Front optical window 11 may include materials that can transmit light in the wavelength range of $\lambda 1$ to $\lambda 2$, with greater absorption in the near infrared band. Optical adapter module 2 may include a plurality of optical lens elements configured to adjust the focal length of anti-fog device 100A. Although anti-fog device 100A is described with the ICG excitation wavelength, it will be appreciated that the anti-fog concept can apply to a fluorescence agent having one or more fluorescence dyes that are currently unknown and will be created or developed in the future.

Anti-fog device 100A also includes a coaxial coupling module 4 and a near infrared (NIR) light blocking filter 5, also referred to as an NIR band-stop filter or an NIR band-rejection filter that passes most wavelengths, but attenuates a specific NIR wavelength range to very low levels. NIR light blocking filter 5 is disposed between elongated member 1 and image sensor 3 along the common optical path 122. Coaxial coupling module 4 may include a semiconductor near infrared (NIR) source 41, a collimator lens or collimator lens group 42, and a dichroic mirror 43. In embodiments where anti-fog device 100A is a visible light only imaging system, semiconductor light source 41 may transmit near infrared light with an emission wavelength range of $\lambda 4$ that can be longer than 700 nm ($\lambda 4 > \lambda 2$) because no NIR imaging, such as ICG, is taking place. In embodiments where anti-fog device 100A is a visible and NIR (ICG) imaging system, semiconductor light source 41 may transmit the near infrared light wavelength range of 24 longer than the wavelength for ICG, i.e., greater than 900 nm.

In some embodiments, semiconductor NIR light source 41 is configured to emit near infrared (NIR) light at a wavelength longer than 780 nm. For the visible light only system (400-700 nm), that NIR wavelength is preferably around the commercially available 808 nm region, because no NIR imaging, i.e., ICG, is taking place. In some other embodiments, semiconductor NIR light source 41 is configured to emit near infrared (NIR) light at a wavelength longer than the wavelength for ICG (which is around 850 nm), such that NIR light source 41 emits an NIR light beam having a wavelength longer than 900 nm. In one embodiment, semiconductor light source 41 may include a laser diode (LD) or a vertical cavity surface emitting laser (VCSEL) device having an output optical power of greater than 1 Watt. Collimator lens group 42 collimates light emitted from semiconductor light source 41 to form a parallel light beam propagating toward dichroic mirror 43. The emission surface of semiconductor light source 41 is located in the vicinity of or at the focal plane of collimating lens or lens group 42. In other words, the LD or VCSEL device is located at or in the vicinity of the focal plane of collimator lens or lens group 42.

Dichroic mirror 43 includes an illumination incident surface 431 facing toward collimator lens group 42, a dichroic surface 432 configured to reflect the parallel light beam collimated by collimator lens group 42 toward elongated member 1 along the common optical path 122, an imaging incident surface 433 facing toward elongated member 1, and an imaging exit surface 434 facing toward image sensor 3. As used herein, the term "incident" refers to a light beam prior to transformation, so an incident surface is the initial area that first receives the light beam.

Illumination incident surface 431 is the incident surface of the near-infrared light on dichroic mirror 43. Dichroic surface 432 is the transmission surface of an imaging light beam 52, which includes reflected light that returns after a visible light beam is irradiated onto an area of interest 51 and reflected from the area of interest, e.g., a surgical field of an endoscope system having visible light only endoscopy. Dichroic surface 432 is also a reflection surface for the near-infrared light having wavelengths longer than 700 nm from semiconductor NIR light source 41 for a visible light only optical imaging system. In an endoscope system having visible light only endoscopy, the visible light beam may be generated by a second semiconductor light source 6. Details of the second semiconductor light source will be described later below. For an endoscope system having visible light and NIR (ICG) light endoscopy, dichroic surface 432 is the transmission surface of an imaging beam including reflected visible light and fluorescence emission light that return from visible and NIR (excitation) light from second light source 6 after irradiating the area of interest by the visible light and NIR (excitation) light emitted by second semiconductor light source 6.

Imaging incident surface 433 is the incident surface of the imaging light beam of the endoscope system on coaxial coupling module 4. Imaging exit surface 434 is the exit surface of the imaging light beam of the endoscope system on coaxial coupling module 4.

Dichroic mirror 43 includes an optical axis Z1 that is an optical path connecting the center of illumination incident surface 431 and the center of dichroic surface 432. Optical axis Z1 is the incident optical axis of the near-infrared light on dichroic mirror 43. Dichroic mirror 43 also includes an optical axis Z2 that is the line or optical path connecting the center of imaging incident surface 433 to the center of dichroic surface 432. Optical axis Z2 is the incident optical axis of the imaging beam of the endoscope system on coaxial coupling module 4. Dichroic mirror 43 further includes an optical axis Z3 that is the line or optical path connecting the center of the imaging light beam of the endoscope system after passing through dichroic surface 432 and the center of imaging exit surface 434. Optical axis Z3 is the exit optical axis of the imaging beam of the endoscope system on coaxial coupling module 4.

In one embodiment, imaging incident surface 433 is parallel to imaging exit surface 434. Imaging incident surface 433 and imaging exit surface 434 are typically perpendicular to illumination incident surface 431. In the embodiment illustrated in FIG. 1, dichroic surface 432 and illumination incident surface 431 form a 45° angle. In embodiments where anti-fog device 100A is a visible light only imaging system, dichroic surface 432 is plated with a dichroic film that reflects light in the wavelength range above 780 nm, preferably around 808 nm and transmits light in the wavelength range of λ1 (400 nm) to λ2 (700 nm). The direction of the reflected light is toward imaging incident surface 433. The optical axis Z1 coincides with the optical axis Z5 of collimator lens group 42.

In one embodiment, NIR light blocking filter 5 is disposed between coaxial coupling module 4 and image sensor 3 along the common optical path 122, i.e., along second and third optical axes Z2 and Z3 since the second and third optical axes Z2 and Z3 and the common optical path 122 are aligned with respect to each other. In embodiments where anti-fog device 100A is a visible light only system, NIR light blocking filter 5 is a filter that transmits light in the wavelength range of λ1 to λ2 and cuts off (blocks) light in the wavelength range longer than 700 nm (e.g., around 808 nm) from light source 41. For example, NIR light blocking filter 5 may be a near infrared light blocking filter. In one embodiment, NIR light blocking filter 5 may have a transmittance less than 0.001 percent in the wavelength longer than 700 nm, preferably longer than 780 nm.

In embodiments where anti-fog device 100A is a visible and NIR (ICG) light system, dichroic surface 432 is plated with a dichroic film that reflects light in the range of 920 nm to 960 nm, preferably 935 nm to 945 nm, and transmits light in the range between about 400 nm and about 900 nm. In some embodiments, the excitation wavelength of semiconductor light source 6 is about 780 nm to 800 nm, and can be 780 nm to 805 nm when LED devices are used for semiconductor light source 6. In one embodiment, the center of the excitation wavelength is at around 789 nm, and the center emission wavelength is around 814 nm with a 40 nm bandwidth (i.e., in a range between 794 nm and 834 nm). In one embodiment, the center of the excitation wavelength may be chosen in the range between 780 nm and 785 nm to compromise the excitation and emission efficiency. In one embodiment, NIR light blocking filter 5 may be a light blocking filter for blocking the ICG excitation wavelengths of 780 nm to 800 nm and the anti-fog wavelengths of semiconductor NIR light source 41 longer than the ICG wavelength (e.g., 850 nm). In another embodiment, NIR light blocking filter 5 may include a first filter configured to block the ICG excitation wavelengths (780 nm-800 nm) and a second filter configured to block the anti-fog wavelengths.

Figure 1B:
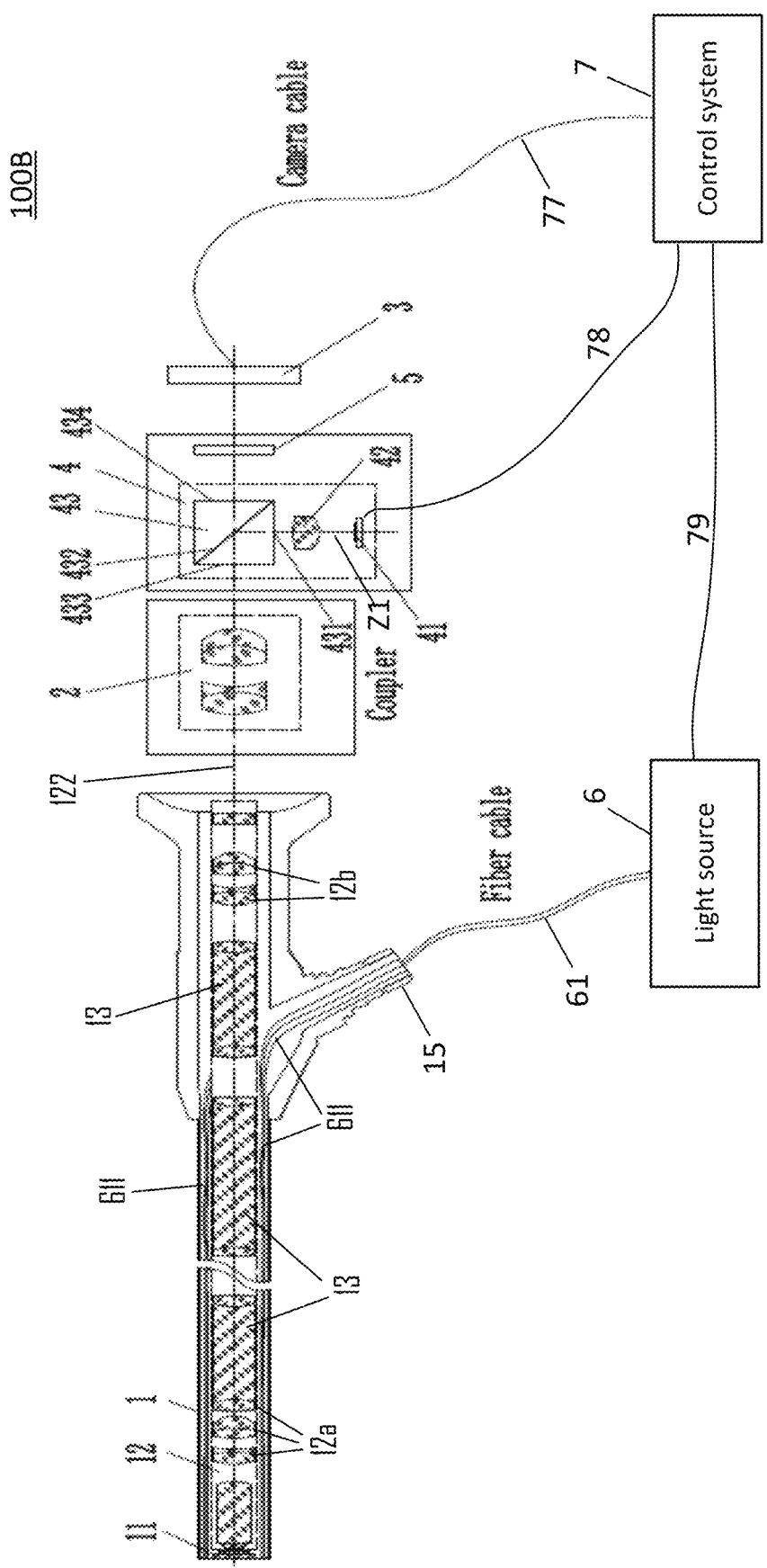
FIG. 1B is a cross-sectional view of an anti-fog device for defogging an endoscope or a medical instrument according to another embodiment of the present disclosure.
Figure 1C:
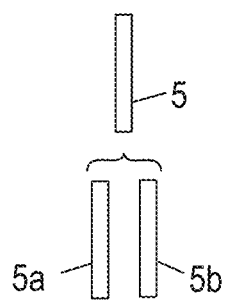
FIG. 1C is a cross-sectional view of an NIR light blocking filter according to an embodiment of the present disclosure.

FIG. 1C is a cross-sectional view of an NIR light blocking filter 5 according to an embodiment of the present disclosure. As shown in FIG. 1C, NIR light blocking filter 5 may include an ICG blocking filter 5a and an anti-fog blocking filter 5b connected in series. While the ICG blocking filter is shown to be in front of the anti-fog blocking filter, it is understood that other configurations are possible, such as the ICG blocking filter is disposed after the anti-fog blocking filter, they can be disposed separated from each other, or assembled together as a single NIR blocking filter.

In one embodiment, front optical window 11 has an absorption greater than 80 percent in the wavelength range from light source 41. An absorption greater than 80 percent allows effective defogging of anti-fog device 100A with a short heating time. It will be appreciated that other absorptions less than 80 percent, for example, 50 percent, 60 percent, 70 percent, could also be utilized in anti-fog device 100A. In such case, the defogging time will be longer. Thus, embodiments of the present disclosure are not limited to an absorption greater than 80 percent. In one embodiment, the optical components (i.e., optical lens elements 12a, 12b, optical guide 13) of optical system 12 and optical adapter module 2 are coated with an antireflection coating in the wavelength range of λ1 to λ4. As an example, the antireflection coating may reflect less than 1 percent of light incident on the antireflection coating. In one embodiment of a visible light only system, semiconductor light source 41 can be an IR laser having an IR wavelength longer than 700 nm, e.g., around 808 nm, the optical components (i.e., optical lens elements 12a, 12b, optical guide 13) of optical system 12 and optical adapter module 2 are coated with an antireflection coating in the wavelength range between about 400 nm and about 850 nm. In one embodiment of a visible and NIR (ICG) light system, the excitation wavelength of an NIR laser of the visible and NIR (ICG) light source (described in more detail below) is around 780 nm and 800 nm, semiconductor light source 41 can be an IR laser having an IR wavelength spectrum around 935 nm and 945 nm, the optical components (i.e., optical lens elements 12a, 12b, optical guide 13) of optical system 12 and optical adapter module 2 are coated with an antireflection coating in the wavelength range between about 400 nm and about 950 nm.

In one embodiment, referring to FIG. 1A, dichroic mirror 43 is shown as having a shape of a cube with the dichroic mirror (i.e., optical coating) in between two prisms. In an exemplary embodiment, two right-angle prisms may be joined together having an optical coating (dichroic mirror) disposed therebetween. In one embodiment, dichroic mirror 43 may be a flat dichroic mirror.

In one embodiment, anti-fog device 100A may further include a second semiconductor light source 6. In one embodiment, second semiconductor light source 6 may include a plurality of LEDs (e.g., a green LED for emitting green light, a blue LED for emitting blue light, and a red LED for emitting red light) for emitting visible light. In some embodiments, output light of the green LED, the blue LED, and the red LED is sent through a fiber cable 61 into elongated member 1 to illuminate target 51. In other embodiments, anti-fog device 100A may be a visible and NIR (ICG) imaging system. In this case, second semiconductor light source 6 may additionally include an NIR light source (e.g., a NIR laser device). In one embodiment, the visible light source (e.g., the red, green, blue LEDs) and the NIR light source are arranged along a same optical axis. A detailed exemplary embodiment for second semiconductor device 6 is provided below with reference to FIGS. 2A and 2B. In one embodiment, fiber cable 61 is attached at an interface section 15 of elongated member 1. In one embodiment, interface section 15 is disposed closed to the proximal end 1b of elongated member 1. Fiber cable 61 includes a plurality of optical fibers 611 that are arranged along the inner surface of elongated member 1. In one embodiment, the plurality of optical fibers 611 are disposed circumferentially around at least a portion of the circumference of front optical window 11 to provide visible light and/or excitation light 53 to target 51. Light 52 reflected from target 51 is transferred through front optical window 11, optical system 12, optical adapter module 2, coaxial coupling module 4 is captured by image sensor 3 and converted to electrical signals. In one embodiment, second semiconductor light source 6 may further include an NIR laser device for observing fluorescence using ICG. The NIR laser device is configured to emit excitation light with wavelengths in an NIR spectrum in a vicinity around 800 nm, e.g., 780 nm to 800 nm for ICG fluorescence imaging. In one embodiment, second semiconductor light source 6 may further include an UV light device emitting UV light with spectrum wavelength about 414 nm. It is noted that light 53 emitting by second semiconductor light source 6 is propagated through optical fibers 611 disposed along the inner surface of elongated member 1 (i.e., outside the front optical window 11), and light 52 reflected from the illuminated target 51 passes through front optical window 11 and optical system 12 along optical axis 122.

FIG. 1B is a cross-sectional view of an anti-fog device 100B for defogging an endoscope, a mechanical or medical instrument according to an embodiment of the present disclosure. Referring to FIG. 1B, anti-fog device 100B includes an elongated member 1, an optical module 2, a coaxial coupling module 4, an NIR light blocking filter 5, and an image sensor 3 arranged sequentially in this order along a common optical axis 122. Elongated member 1 may include an endoscope or laparoscope system or a part of an endoscope or laparoscope system and contain a front optical window 11 and an optical system 12. In some embodiments, optical system 12 may include a plurality of optical lens elements and one or more optical guides 13. In one embodiment, the plurality of optical lens elements may include a set of distal lens elements 12a and a set of proximal lens elements 12b disposed on opposite ends of elongated member 1. The one or more optical guides 13 and the plurality of optical lens elements 12a, 12b are disposed along the optical axis 122. Coaxial coupling module 4 includes a first semiconductor light source 41, a collimator lens or collimator lens group 42, and a dichroic mirror 43 arranged along an optical axis Z1. First semiconductor light source 41 may include a laser diode (LD) or vertical cavity surface emitting laser (VCSEL) device having an output optical power of greater than 1 Watt and located in the vicinity of or at the focal plane of collimator lens 42.

Anti-fog device 100B can support at least two imaging systems: a visible light only imaging system, a visible light and NIR excitation light (e.g., ICG) imaging system. In embodiments for a visible light only imaging system, first semiconductor light source 41 is configured to emit near infrared light wavelengths longer than 700 nm. In embodiments for a visible light and NIR excitation light (e.g., ICG) imaging system, first semiconductor light source 41 emits NIR wavelength in the range between 900 nm and 1300 nm, and more preferably between 900 nm and 1000 nm. Anti-fog device 100A and anti-fog device 100B can have similar structures. In the example shown in FIG. 1B, a common control system is shown in anti-fog device 100B for controlling the different components. But it is understood that first semiconductor light source 41, second semiconductor light source 6, and image sensor 3 each can have its own controller. The exemplary descriptions below are intended to facilitate an understanding of the present disclosure and are not limiting.

Dichroic mirror 43 includes an illumination incident surface 431 facing toward collimator lens group 42, a dichroic surface 432 configured to reflect the parallel light beam collimated by collimator lens group 42 toward elongated member 1 along the common optical path 122, an imaging incidence surface 433 facing toward elongated member 1, and an imaging exit surface 434 facing toward image sensor 3.

In one embodiment, anti-fog device 100B further includes a second semiconductor light source 6 coupled to elongated member 1 through a fiber cable 61 at an interface section 15 of elongated member 1. Fiber cable 61 may include a plurality of optical fibers 611 disposed along the inner surface of elongated member 1. Second semiconductor light source 6 is configured to generate visible light (e.g., ~ 400 nm-700 nm) as well as NIR excitation light with wavelengths in the vicinity around 800 nm (e.g., ~ 780 nm-800 nm). Second semiconductor light source 6 can be operated in different modes depending on the imaging modes. As described more fully below, second semiconductor light source 6 is operable to output both visible light and NIR light, with independent control over each of the wavelength regions. In one embodiment, second semiconductor light source 6 can output NIR light with no visible light. In one embodiment, second semiconductor light source 6 can output visible light with no NIR light. In one embodiment, second semiconductor light source 6 can output both visible light and NIR light concurrently. In one embodiment, second semiconductor light source 6 can output visible light with no NIR light. In one embodiment, second semiconductor light source 6 can output both visible light and NIR light concurrently and continuously. The output light from second semiconductor light source 6 is sent through fiber cable 61 into the optical fibers 611 along elongated member 1 to illuminate a target disposed in the vicinity of the front optical window 11. The reflected visible light and the excited fluorescent emission with a second NIR spectrum (e.g., ~ 790 nm-850 nm, preferably 814 nm with a 40 nm bandwidth) are received by anti-fog device 100B to be imaged by image sensor 3.

In one embodiment, anti-fog device 100B also includes a control system 7 having a camera cable 77 coupled to image sensor 3, a first control cable 78 coupled to first semiconductor light source 41, and a second control cable 79 coupled to second semiconductor light source 6. Control system may include an image display device or a monitor, e.g., a liquid crystal display (LCD) configured to produce an image from electrical signals received from image sensor 3, an input port configured to receive inputs from a user, and a power supply module configured to supply power to components of anti-fog device 100B, i.e., power to image sensor 3, first semiconductor light source 41, and second semiconductor light source 6. Control system 7 may include a plurality of individual control boxes containing one or more controllers. For example, control system may include a first control box including at least one controller or processor coupled to image sensor 3, a second control box including at least one controller or processor coupled to first semiconductor light source 41, and a third control box including at least one controller or processor coupled to second semiconductor light source 6. The first control box is configured to process the electrical signals received from image sensor 3, and the second and third control boxes are configured to control intensity of the reflected visible light and intensity of the first and second semiconductor light sources, respectively. Control system 7 and the controller boxes will be described in more detail below.

In one embodiment, coaxial coupling module 4 is located between adapter optical system 2 and NIR light blocking filter 5, as shown in FIGS. 1A and 1B. Referring to FIGS. 1A and 1B, anti-fog devices 100A and 100B each include an elongated member 1, an optical adapter module 2, a coaxial coupling module 4, an NIR light blocking filter 5, and an image sensor 3 arranged sequentially in this order. Of course, other variations and alternatives are possible without departing from the scope of the present disclosure.

Figure 2A:
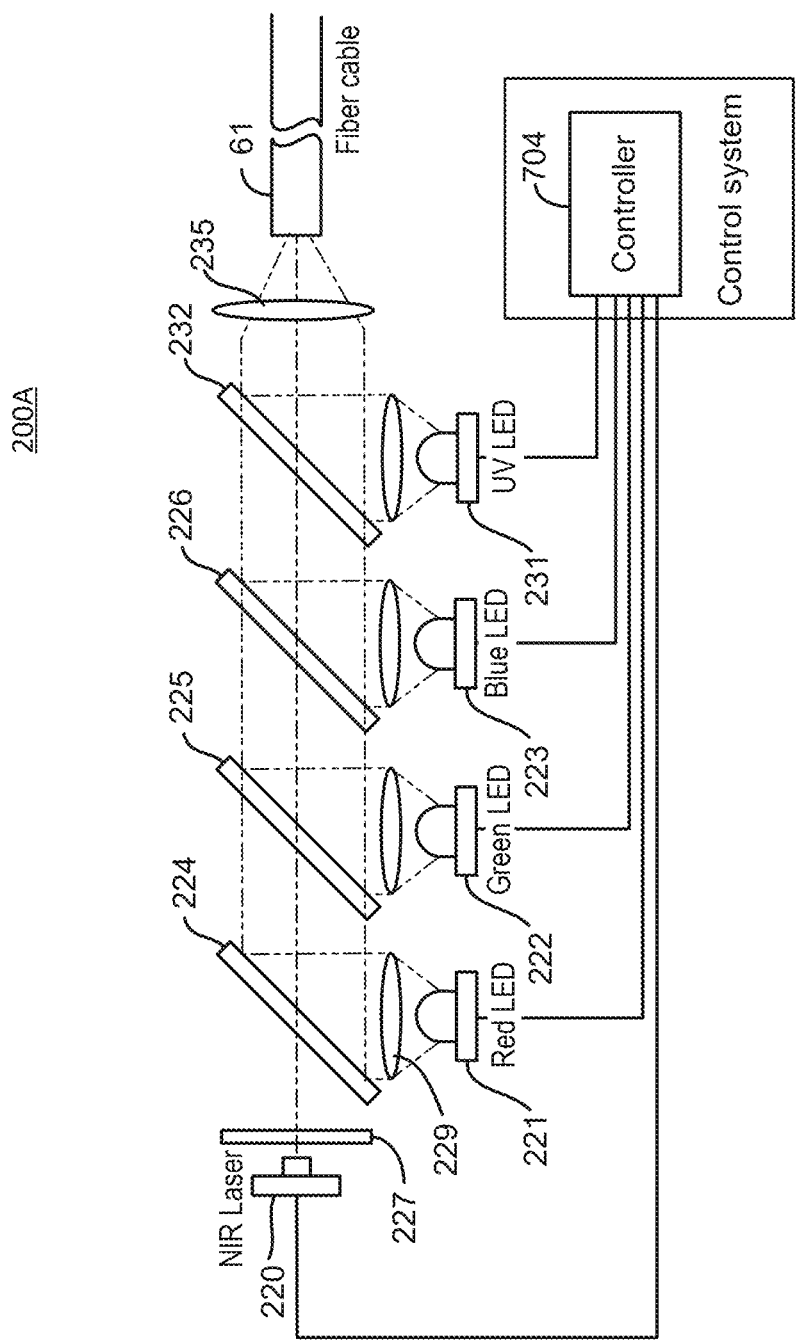
FIG. 2A is a simplified schematic diagram of a second semiconductor light source for an anti-fog device according to an embodiment of the present disclosure.

FIG. 2A is a simplified schematic diagram of a second semiconductor light source 200A for an anti-fog device according to an embodiment of the present disclosure. Second semiconductor light source 200A may be the second light source 6 of FIG. 1A and FIG. 1B. Referring to FIG. 2A, a NIR laser 220 generates excitation light with wavelengths in an NIR spectrum (e.g., 780 nm-800 nm). In some embodiments, NIR laser 220 is a semiconductor laser, but other lasers, LEDs, VCSEL, and the like can be utilized. The excitation light from NIR laser 220 passes through laser-line filter 227 that is characterized by a very narrow passband (e.g., 10 nm wide). Laser-line filter 227 transmits the desired excitation wavelengths while suppressing side-band radiation.

In the embodiment illustrated in FIG. 2A, a plurality of visible light sources, for example, red LED 221, green LED 222, and blue LED 223 provide light that is used to generate the visible light emission used in the anti-fog device. Red light from red LED 221, green light from green LED 222, and blue light from blue LED 223 are combined using an appropriate ratio of the light intensity from each source to form white light as described more fully below. Color combiners 224, 225, and 226 combine the light from NIR laser 220 as well as the light from red LED 221, green LED 222 and blue LED 223 to form the multi-spectral output that is input into the anti-fog device through fiber cable 61. In one embodiment, second semiconductor light source 200A may also include an optical lens 229 disposed in front of each of the red, green, and blue LEDs and configured to collimate light emitted from the LEDs to the color combiners.

In some embodiments, second semiconductor light source 200A may also include an ultraviolet (UV) light emitting diode or laser diode 231 and a UV light combiner 232 that combined UV light with the light from NIR laser or LED 220 and the light from red LED 221, green LED 222 and blue LED 223 to form the multi-spectral output that is input into the anti-fog device through fiber cable 61. As illustrated in FIG. 2A, the combined light from the NIR light source and visible light sources is coupled by optical lens 235 into fiber cable 61 and then provided to the anti-fog device for illumination. NIR laser 220, red LED 221, green LED 222, blue LED 223, and/or UV LED or laser diode 231 can be disposed together in a light source, e.g., second semiconductor light source 6 shown in FIGS. 1A and 1B.

NIR laser 220, red LED 221, green LED 222, blue LED 223, and/or UV LED or laser diode 231 are each independently controlled by a controller 704. Through the use of the controller, the intensity of the NIR excitation light, the intensity of the visible light and/or the UV light can be adjusted, for example, by changing the driving current provided to the NIR laser and the LEDs. In one embodiment of the anti-fog device, the intensity of the visible light is adjusted (e.g., attenuated) in order to achieve the desired contrast between the fluorescence image and the visible light image. Additional optical approaches, such as the use of neutral density filters, or electrical approaches, such as modulation methods, can be applied to attenuate the visible light significantly and/or adjust the light intensity with the desired precision.

In one embodiment, red LED 221 may be a red-amber LED. In some embodiments, second semiconductor light source 200A may include a combination of brightness signals RYGB and NIR excitation light. In an exemplary embodiment, second semiconductor light source 200A may include a photoelectric conversion device that generate brightness signals RYGB according to predetermined coefficients of the red, green, and blue color components. In other embodiments, second semiconductor light source 200A may include a combined excitation light in an NIR wavelength and a white light source. In some embodiments, the white light may include four primary colors, such as red, yellow, green, and blue, denoted as RYGB. In some other embodiments, red LED 221, green LED 222, blue LED 223 may be replaced by one or more white LED devices. The present disclosure is not limited to a particular embodiment. Alternate embodiments will be apparent to persons skilled in the art based on the teachings contained herein. It will be appreciated that the positions of the red, green, blue, and UV LEDs can be interchanged with each other without affecting the operations of the second semiconductor light source.

Figure 2B:
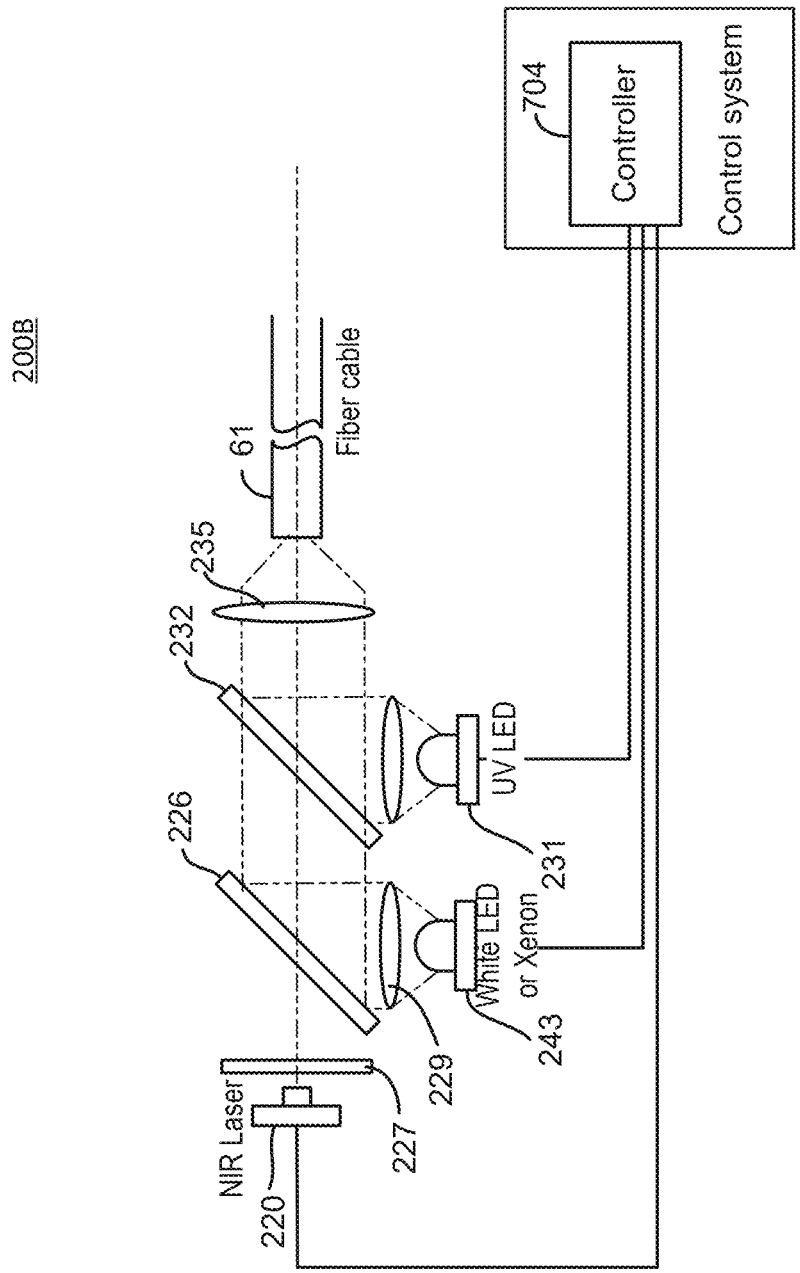
FIG. 2B is a simplified schematic diagram of a second semiconductor light source for an anti-fog device according to another embodiment of the present disclosure.

FIG. 2B is a simplified schematic diagram of a second semiconductor light source 200B for an anti-fog device according to another embodiment of the present disclosure. Second semiconductor light source 200B may be the second light source 6 of FIG. 1A and FIG. 1B. Referring to FIG. 2B, a NIR laser 220 generates excitation light with wavelengths in an NIR spectrum (e.g., 780 nm-800 nm). In some embodiments, NIR laser 220 is a semiconductor laser, but other lasers, LEDs, VCSEL, and the like can be utilized. The excitation light from NIR laser 220 passes through laser-line filter 227 that is characterized by a very narrow passband (e.g., 10 nm wide). Laser-line filter 227 transmits the desired excitation wavelengths while suppressing side-band radiation.

In the embodiment illustrated in FIG. 2B, a white light source 243 provides light that is used to generate the visible light emission used in the anti-fog device. White light source 243 may include one or more white LED devices continuously or time sequentially emitting white light or a Xenon light source continuously emitting illumination light. Color combiner 226 combines the light from NIR laser 220 as well as the light from white light source 243 to form the multi-spectral output that is input into the anti-fog device through fiber cable 61. In one embodiment, second semiconductor light source 200B may also include an optical lens 229 disposed in front of white light source 243 and configured to collimate light emitted from white light source 243 to color combiner 226.

In some embodiments, second semiconductor light source 200B may also include an ultraviolet (UV) light emitting diode or laser diode 231 and a UV light combiner 232 that combined UV light with the light from NIR laser or LED 220 and the light from white light source 243 to form the multi-spectral output that is input into the anti-fog device through fiber cable 61. In one embodiment, an optical lens 229 may be disposed in front of UV light and configured to collimate UV light emitted from UV LED or UV laser diode 231. As illustrated in FIG. 2B, the combined light from the NIR light source and white light source is coupled by optical lens 235 into fiber cable 61 and then provided to the anti-fog device for illumination.

NIR laser 220, white light source 243, and/or UV LED or laser diode 231 are each independently controlled by a controller 704 residing in a control system (e.g., control system 7 of FIG. 1B). Through the use of the controller, the intensity of the NIR excitation light and the intensity of the white light can be adjusted, for example, by changing the driving current provided to the NIR laser and the LEDs. In one embodiment of the anti-fog device, the intensity of the white light is adjusted (e.g., attenuated) in order to achieve the desired contrast between the fluorescence image and the visible light image. Additional optical approaches, such as the use of neutral density filters, or electrical approaches, such as modulation methods, can be applied to attenuate the visible light significantly and/or adjust the light intensity with the desired precision. It will be appreciated that the positions of the white light source and the UV LED are interchangeable as required.

Figure 3:
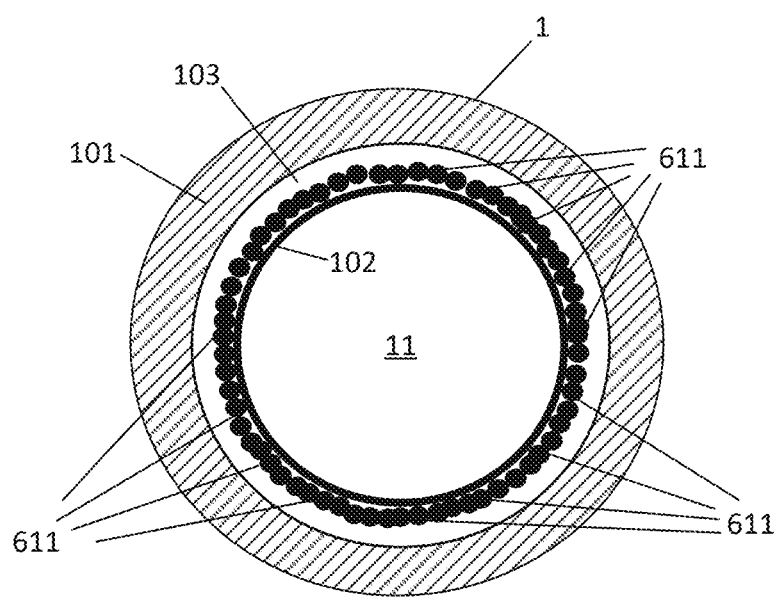
FIG. 3 is a diagram illustrating a front view of an elongated member according to some embodiments of the present disclosure.

FIG. 3 is a diagram illustrating a front view of an elongated member 1 according to some embodiments of the present disclosure. Referring to FIG. 3, elongated member 1 includes an outer tube 101 and an inner hollow tube 102 axially disposed relative to outer tube 101. A plurality of optical fibers 611 are uniformly and densely distributed in a space (air gap) 103 between outer tube 101 and inner hollow tube 102 of elongated member 1. In one embodiment, optical fibers 611 are fully or completely packed (filled) space or air gap 103. Front optical window 11 is also shown. In the example shown in FIG. 3, optical fibers 611 are shown to be arranged in a single layer along an outer periphery of inner hollow tube 102, however, it is understood that more than one layer of optical fibers can be uniformly arranged for completely filling the air gap between the outer tube and the inner hollow tube. For example, the plurality of optical fibers can be fully packed tightly together in one or more layers filling the space between the outer tube and inner hollow tube. In practical applications, hundreds of individual fiber (e.g., glass strands) are evenly and densely distributed on inner hollow tube 102. It is also noted that the dimensions of the optical fibers and the cross-section of elongated member 1 are exaggerated relative to each other for clarity. Optical system 12 is disposed in the hollow portion of inner tube 102 facing the backside of front optical window 11.

Figure 4A:
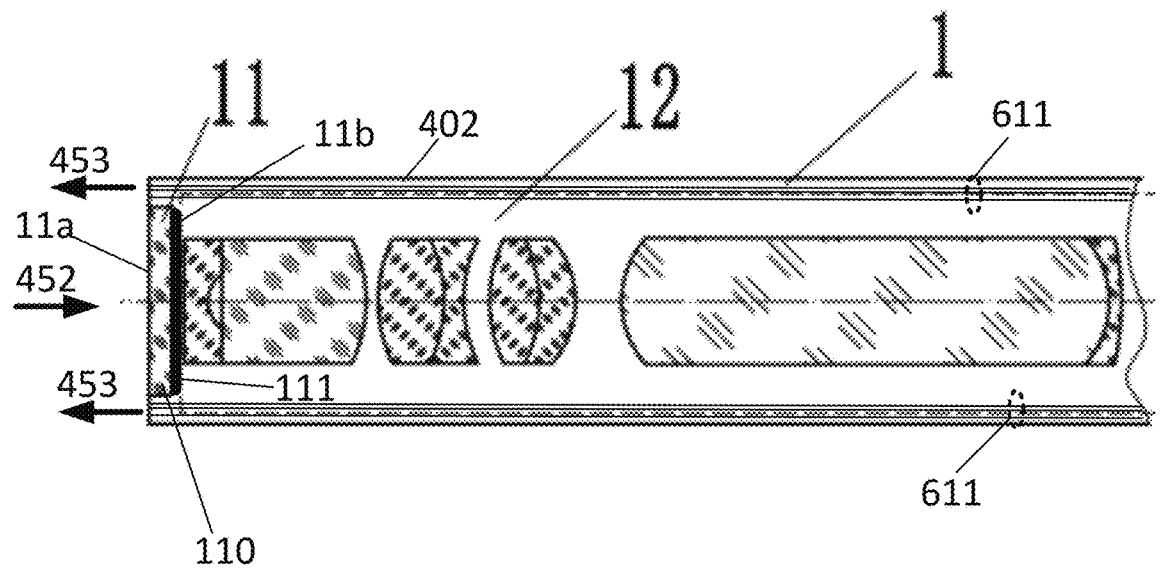
FIGS. 4A through 4C are cross-sectional views of an enlarged portion of an elongated member having a near-infrared (NIR) light-absorbing optical window including a sapphire substrate with an NIR-absorption glass plate, a doped sapphire substrate, and a sapphire substrate having an NIR-absorption coating, respectively, according to embodiments of the present disclosure.

FIG. 4A is a cross-sectional view of an enlarged portion of an elongated member 1 having a near-infrared (NIR) light-absorbing optical window 11 according to an embodiment of the present disclosure. Referring to FIG. 4A, light (visible light and/or NIR excitation light) 453 emitting by second semiconductor light source 6 (not shown) is propagated through optical fibers 611 disposed along a periphery of an inner hollow tube 402 of elongated member 1 to illuminate a target area. NIR light-absorbing optical window 11 includes a sapphire glass or sapphire substrate 110 having first surface 11a facing away from elongated member 1, a second surface 11b facing toward optical system 12, and a glass plate 111 disposed on second surface 11b of sapphire substrate 110. In one embodiment, glass plate 111 is attached (e.g., using an adhesive) or otherwise joined to the second surface of NIR light-absorbing optical window 11 and configured to allow transmission of reflected light 452 (reflected visible light and/or fluorescence emission from a target area) while absorbing infrared and near infrared light emitted from first semiconductor light source 41. It is understood that elongated member 1 can be utilized for both the visible light only endoscopy system and the visible light plus IR (ICG) endoscope system.

Figure 4B:
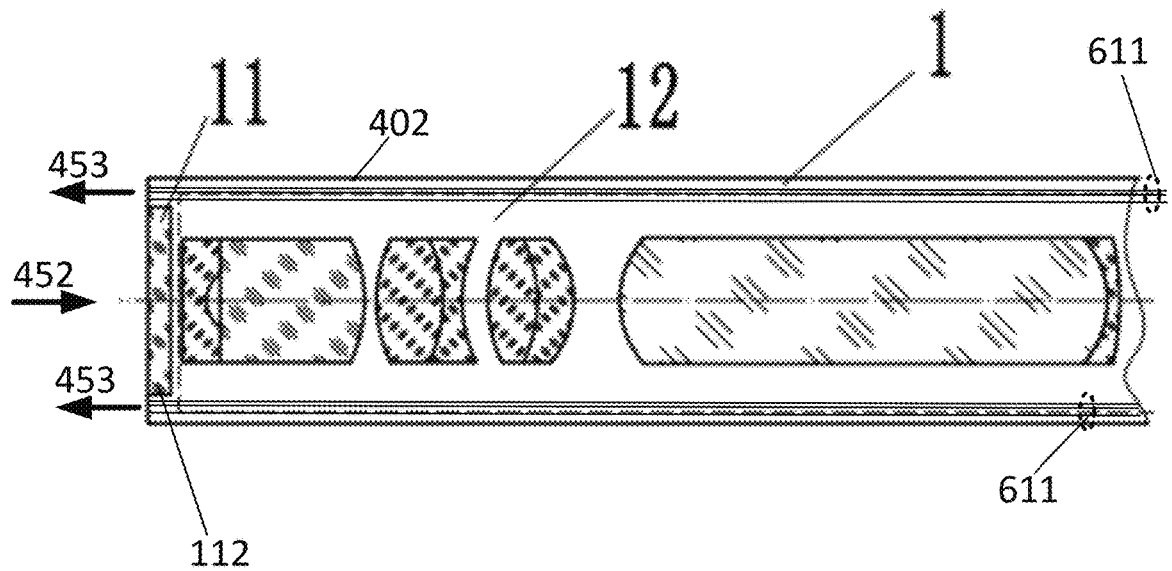
Figure 4C:
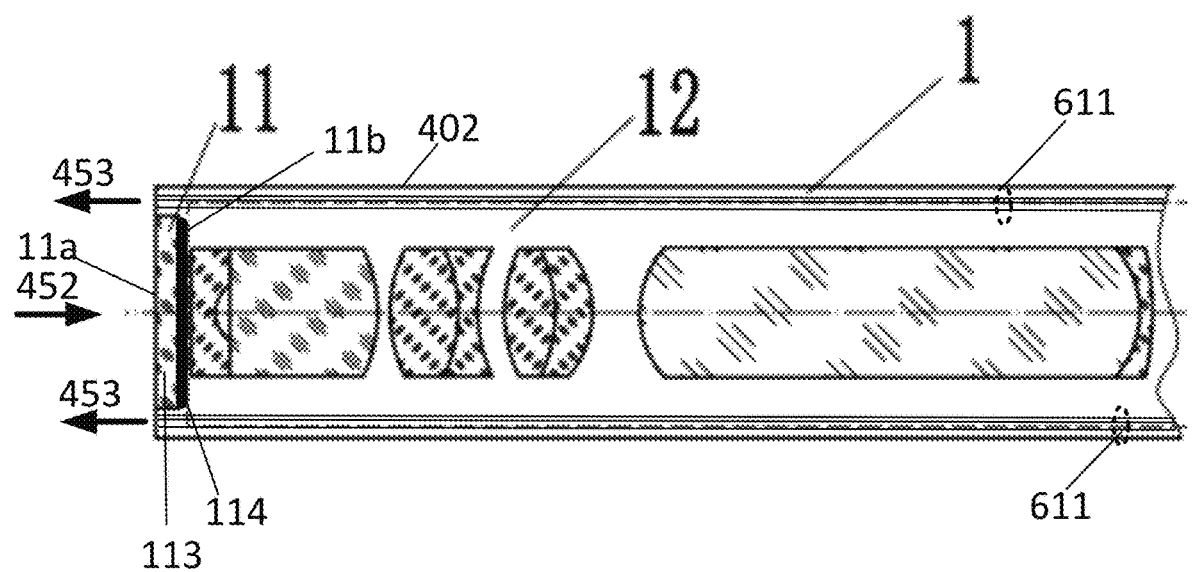

FIG. 4B is a cross-sectional view of an enlarged portion of an elongated member 1 having a near-infrared (NIR) light-absorbing optical window 11 according to an embodiment of the present disclosure. Similar to the embodiment illustrated in FIG. 4A, light (visible light and/or NIR excitation light) 453 emitting by second semiconductor light source 6 (not shown) is propagated through optical fibers 611 disposed along an inner hollow tube 402 of elongated member 1 to illuminate a target area. In this embodiment, NIR light-absorbing optical window 11 includes a sapphire glass 112 doped with impurities that have the properties of transmitting visible light incident on NIR light-absorbing optical window 11 while absorbing IR light emitted from first semiconductor light source 41 and thus heating up when irradiated with IR light. In one embodiment, sapphire glass 112 is doped with ytterbium (Yb) and erbium (Er). It is understood that this embodiment can be utilized for both the visible light only endoscopy system and the visible light plus IR (ICG) endoscope system FIG. 4C is a cross-sectional view of an enlarged portion of an elongated member 1 having a near-infrared (NIR) light-absorbing optical window 11 according to an embodiment of the present disclosure. Similar to the embodiment illustrated in FIG. 4A, light (visible light and/or NIR excitation light) 453 emitting by second semiconductor light source 6 (not shown) is propagated through optical fibers 611 disposed along an inner hollow tube 402 of elongated member 1 to illuminate a target area. Referring to FIG. 4C, in one embodiment, NIR light-absorbing optical window 11 may include a sapphire glass 113 having a heat absorption coating 114 deposited on second surface 11b facing toward optical system 12. In one embodiment, heat absorption coating 114 may be deposited using physical vapor deposition (PVD) or a chemical vapor deposition (CVD) process. ITO and other materials that will absorb at infrared wavelengths and transmit light at visible wavelength ranges can be used. It will be appreciated that the various embodiments of the elongated member can be utilized for both the visible light only endoscopy system and the visible light plus IR (ICG) endoscope system.

Figure 5:
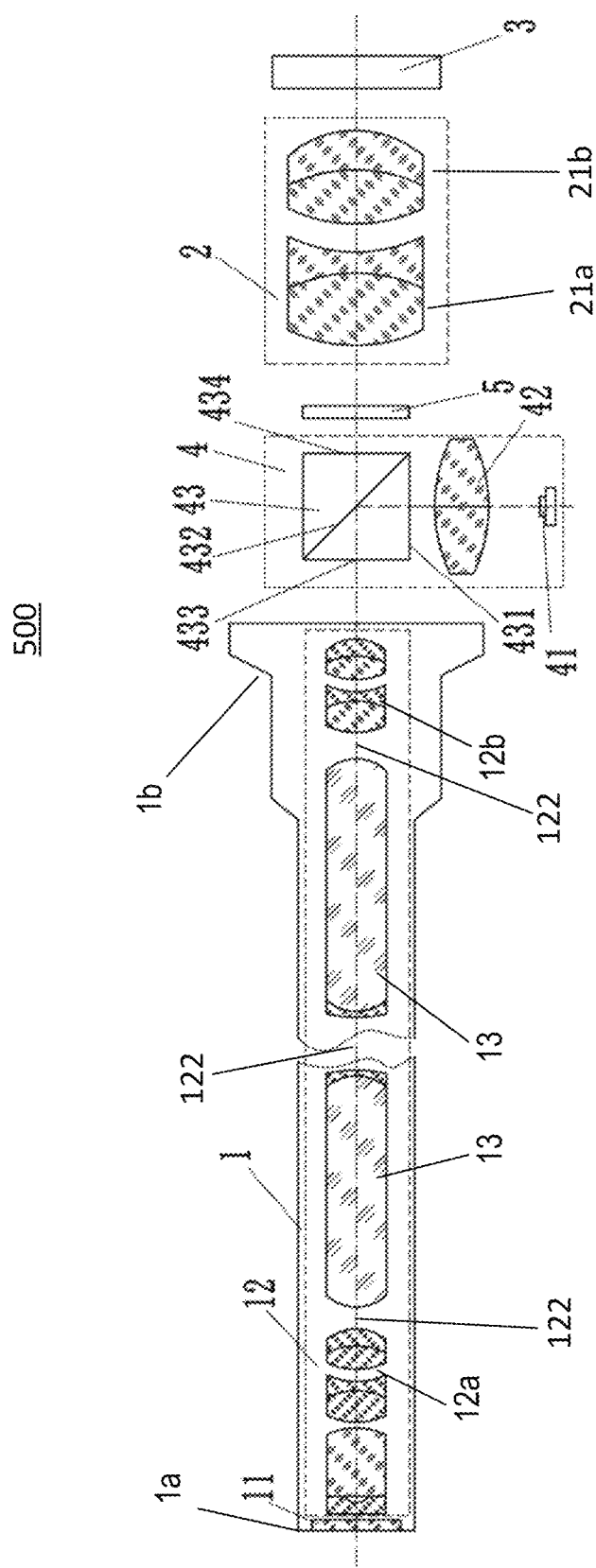
FIG. 5 is a cross-sectional view of an anti-fog device for defogging an endoscope or a medical instrument according to another embodiment of the present disclosure.

An alternative implementation of an anti-fog device 500 for defogging an endoscope or a medical instrument is shown in FIG. 5. FIG. 5 illustrates a cross-sectional view of an anti-fog device 500 for defogging an endoscope or a medical instrument according to another embodiment of the present disclosure. Referring to FIG. 5, anti-fog device 500 is substantially similar to anti-fog device 100A except for the differences described herein. Accordingly, description provided in relation to the elements illustrated in FIG. 1A is applicable to the elements illustrated in FIG. 5 as appropriate.

Specifically, as shown in FIG. 5, coaxial coupling module 4 is disposed between optical system 12 and optical adapter module 2. As described above, optical adapter module 2 may include a plurality of optical lens elements 21a, 21b for adjusting focal length variations in the optical components of optical system 12 and adjusting the focal length of device 500. Similarly, elongated member 1 has a hollow body with a distal end 1a having a near-infrared light-absorbing optical window 11 and a proximal end 1b, and optical system 12 is disposed between near-infrared light-absorbing optical window 11 and proximal end 1b. Optical system 12 may include a plurality of optical lens elements 12a, 12b and one or more optical guides 13, which may be a part of an endoscope, a medical instrument, or a viewing system. It should be noted that although NIR light blocking filter 5 is shown as disposed between coaxial coupling module 4 and optical adapter member 2, other variations and alternatives are also possible. For example, in one embodiment, NIR light blocking filter 5 may be placed between optical adapter member 2 and image sensor 3. In one embodiment, optical system 12 includes an endoscope or a part of an endoscope system. Light source 6 and control system 7 are not shown for the sake of clarity. The embodiments of anti-fog devices 100A, 100B, and 500 shown in respective FIGS. 1A, 1B, and 5 differ in the location of the optical coupling module. These embodiments are presented for purposes of illustration and are not intended to limit the present disclosure. Alternate embodiments, differing from those described herein, will be apparent to persons skilled in the art based on the teachings contained herein.

Figure 6:
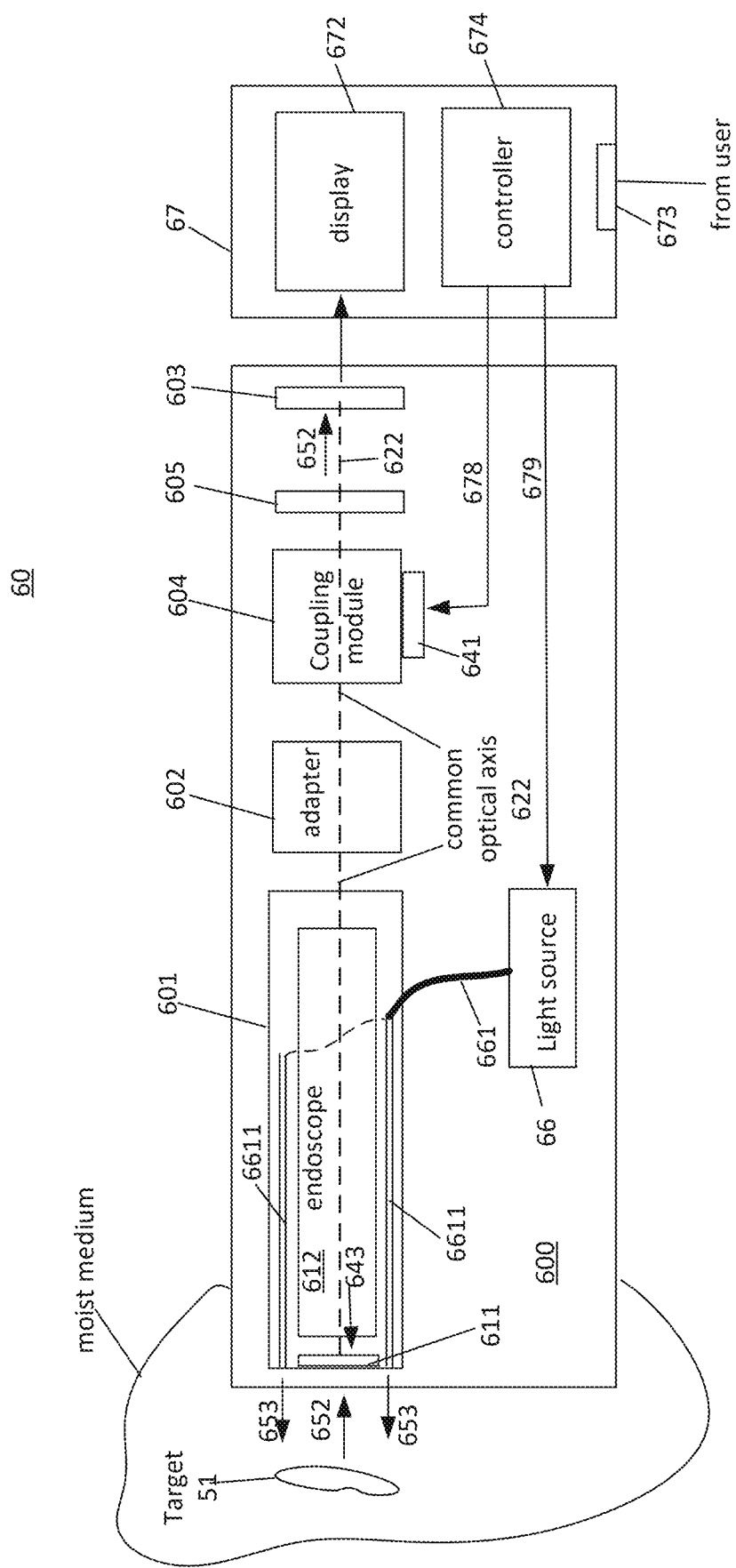
FIG. 6 is a simplified schematic diagram of a basic fog-free optical imaging system according to some embodiments of the present disclosure.

FIG. 6 is a simplified schematic diagram of a basic fog-free optical imaging system 60 according to some embodiments of the present disclosure. The basic fog-free optical imaging system 60 may include anti-fog devices 100A, 100B of FIGS. 1A and 1B or anti-fog device 500 of FIG. 5. As described herein, embodiments of the present disclosure are particularly useful for defogging endoscopes or medical and viewing instruments that are inserted into the inside of a moist medium, where a user needs a fog-free image of the moist medium (e.g., a tissue) under examination. Fog-free optical imaging system 60 includes an optical imaging device 600, and a control system 67 coupled to optical imaging device 600. Optical imaging device 600 includes an elongated member 601 having a hollow body for receiving an endoscope 612, an optical adapter module 602 for adjusting a focal length of optical imaging device 600 due to focal length variations of the optical components in the endoscope and variation of an image sensor location, a coaxial coupling module 604, an NIR light blocking filter 605, and an image sensor 603. Control system 67 may include an image display device 672 coupled to image sensor 603, an input port 673 for receiving inputs or instructions from a user, and at least one controller 674 for providing control signals 678, 679 to different semiconductor light sources 641 and 66. In one embodiment, the at least one controller 674 may include a plurality of individual controllers configured to provide control signals 678 and 679 to semiconductor light sources 641 and 66. Semiconductor light source 66 may be the semiconductor light source 200A or 200B shown and described with reference to FIGS. 2A and 2B. In one embodiment, semiconductor light source 66 may emit visible light and NIR light for ICG (780 nm-800 nm). In another embodiment, semiconductor light source 66 may emit visible light, NIR light for ICG, and UV light. Light emitted by semiconductor light source 66 is provided to a plurality of optical fiber strands 6611 through a fiber cable 661. Optical fiber strands 6611 are disposed circumferentially around elongated member 601 and front optical window 611 and provide light 653 to illuminate target 51. In one embodiment, elongated member 601 may be similar or the same as the elongated member described and illustrated in FIG. 3. Although the basic fog-free optical imaging system 60 is described for an endoscope, it is understood that the fog-free optical imaging system 60 may be used for a wide variety of medical and/or surgical instruments, such as laparoscopes, cystoscopies, and other minimally invasive surgical applications.

Elongated member 601 has a front optical window 611 for receiving an NIR light beam 643 emitted by semiconductor light source 641. In some embodiments, semiconductor light source 641 is disposed in coaxial coupling module 604. In other embodiments, semiconductor light source 641 is coupled to coaxial coupling module 604 through a collimator device (not shown). Coaxial coupling module 604 and semiconductor light source 641 may be respective coaxial coupling module 4 and semiconductor light source 41 shown and described in detail with respect to FIG. 1A, so that a description thereof is omitted herein for the sake of brevity. An exemplary structure of front optical window 611 has been described in detail above with reference to FIGS. 4A to 4C. In some embodiments, the position of coaxial coupling module 604 and optical adapter module 602 can be interchanged. For example, coaxial coupling module 604 may be placed between elongated member 601 and optical adapter module 602. In other words, the components of optical imaging device 600 having a common optical axis are not fixedly connected together and are interchangeable. Components of elongated member 601 including endoscope (laparoscope, cystoscopies) 612, optical adapter module 602, coaxial coupling module 604, NIR light blocking filter 605, and an image sensor 603 are aligned along a common optical axis 622.

Image sensor 603 receives reflected visible light and/or NIR fluorescent light 652 from an area of interest 51 in a moist medium. Visible light and/or NIR fluorescent light 652 passes through coaxial coupling module 604 and NIR light blocking filter 605 and arrives at image sensor 603. Image sensor 603 converts light 652 into electrical signals that can be displayed by image display device 672 in control system 67. Controller 674 is coupled to semiconductor light source 641 and configured to control an illumination duration of an NIR light beam 643 emitted by semiconductor light source 641 to heat up front optical window 611.

In some embodiments, controller 674 turns on semiconductor light source 641 for a predetermined time duration that has a range between 3 seconds and 50 seconds, preferably between 5 seconds and 40 seconds, and more preferably between 10 seconds and 30 seconds. In other embodiments, controller 674 turns on semiconductor light source 641 based on an algorithm. For example, controller 674 may perform a frame-to-frame comparison to determine how much clearer an image has become between frames and calculate a time duration of NIR light illumination based on comparison data. In addition to frame-to-frame comparisons, comparisons may be performed using a set of frames other than consecutive frames. In yet other embodiments, controller 674 may have an input port 673 configured to receive instructions or inputs from a user or operator to turn on and turn off semiconductor light source 641. Input port 673 may support wire (e.g., USB, I2C) and wireless (e.g., Bluetooth, WiFi) standards that are commonly used in the computer and communication industries and other proprietary communication protocols.

In accordance with a first exemplary embodiment of a visible light only imaging system, semiconductor light source 41 includes a laser diode (LD) with emitted wavelengths longer than 700 nm, preferably in the wavelength range between 805 nm and 810 nm and emitted output power of about 1 Watt. Front optical window 11 has an absorption rate that is around 80% at wavelengths 805 nm-810 nm. Optical system 12 and optical adapter module 2 have an imaging wavelength range from about 400 nm to about 700 nm to pass visible light. The optical components of optical system 12 and the adapter optical module 2 are coated with an antireflection coating in the wavelength range from about 400 nm to about 810 nm. Dichroic mirror 43 may include a plurality of prisms. In one embodiment, dichroic mirror 43 may include right triangular prisms bonded together. In one embodiment, the prisms are bonded together using an adhesive. The dichroic film on the dichroic surface 432 reflects incident wavelengths from about 805 nm to about 810 nm and transmits wavelengths in the range from about 400 nm to about 700 nm. Coaxial coupling module 4 is located between adapter optical module 2 and image sensor 3, as shown in FIGS. 1A and 1B. NIR light blocking filter 5 transmits (passes) wavelengths in the range from about 400 nm to about 700 nm and has a transmittance of less than 0.001% for wavelengths of 805 nm-810 nm. NIR light blocking filter 5 is located between coaxial coupling module 4 and image sensor 3.

Near-infrared (NIR) light with wavelengths of 805 nm to 810 nm is emitted by the LD and passes through collimating lens group 42 to form a slightly divergent NIR light beam. The degree of divergence is consistent with the degree of convergence of the optical imaging system after passing through optical adapter module 2. After the NIR light beam is incident on dichroic surface 432, following the principle of reversibility of light, it will reflect from dichroic surface 432 and enter optical adapter module 2. After passing through optical adapter module 2 and optical system 12, this reflected NIR light beam will be irradiated onto front optical window 11. The inventors have observed that 1 Watt of near infrared light will result in an optical power irradiated onto front optical window 11 of about 0.5 Watt. As a result of absorption of near infrared light by front optical window 11, the temperature of front optical window 11 will increase. The inventors have further observed that the temperature of front optical window 11 can increase from room temperature 20° C. to 37° C. within one (1) minute. It is noted that the room temperature 20° C. is approximately the room temperature in an operational room, and the temperature of 37° C. is approximately the temperature of a human body. During this time, no fog will develop in optical system 12 while the optical system is inserted into the inside of a moist medium, such as moist tissue. An imaging light beam of wavelengths in the range from about 400 nm to about 700 nm will pass through optical system 12, optical adapter module 2, and imaging incident surface 433 of dichroic mirror 43 and be incident on dichroic surface 432, which can be optically coated with a dichroic film that reflects light in wavelengths in the range from about 805 nm to about 810 nm and transmits wavelengths in the range from about 400 nm to about 700 nm. The imaging light beam of wavelengths in the range from about 400 nm to about 700 nm will pass through dichroic surface 432, exit imaging exit surface 434, and arrive at NIR light blocking filter 5. Since NIR light blocking filter 5 transmits light in the wavelength range between about 400 nm and about 700 nm and blocks wavelengths in the range of about 805 nm to about 810 nm, the imaging light beam without the NIR light of 805 nm-810 nm will finally converge on image sensor 3, which converts the imaging light beam into electrical signals. Since image sensor 3 is provided with NIR light blocking filter 5 that cuts off (blocks) light in the wavelength range of 780 nm-810 nm, which is the excitation light emitted by the LD, even if the NIR light emitted by the LD enters the optical system and the adapter optical module due to reflection, the NIR light cannot reach the image sensor, so the image quality will not be affected. While the first exemplary embodiment describes the configuration with reference to FIGS. 1A and 1B, the visible light only imaging system may also be applied to the configuration shown in FIG. 5.

In accordance with a second exemplary embodiment, semiconductor light source 41 includes a vertical cavity surface emitting laser (VCSEL) with emitted wavelengths of ~ 935 nm-945 nm and emitted output power of about 2 W. Front optical window 11 has an absorption rate of about 80% for wavelengths of ~ 935 nm-945 nm. Optical system 12 has an imaging wavelength in the range from about 400 nm to about 900 nm. The optical components of optical system 12 is coated with an antireflection coating in the wavelength range of 400 nm to 945 nm. Dichroic mirror 43 is a planar dichroic mirror and has a dichroic film disposed on dichroic surface 432 that reflects light in the wavelength range from about 935 nm to about 945 nm and transmits wavelengths of about 400 nm to about 900 nm. Coaxial coupling module 4 is located between optical system 12 and optical adapter module 2, as shown in FIG. 5. NIR light blocking filter 5 passes light in the wavelength range from about 400 nm to about 900 nm and has 0.001% transmission for wavelengths of ~ 935 nm-945 nm. NIR light blocking filter 5 is located between coaxial coupling module 4 and optical adapter module 2, as shown in FIG. 5. NIR light blocking filter 5 is configured to block both the wavelength spectrum of excitation light and the wavelength spectrum of the anti-fog laser. In one embodiment, NIR light blocking filter 5 may include an ICG blocking filter 5a and an anti-fog blocking filter 5b connected in series, as shown in FIG. 1C.

The working principle of the second exemplary embodiment is similar to that of the first exemplary embodiment. After the NIR light beam of wavelengths in the range of ~ 935 nm-945 nm emitted by the VCSEL 41 is incident on dichroic surface 432, following the principle of reversibility of light, it will be reflected and exit from imaging incident surface 433 and enter optical system 12. After passing through optical system 12, this reflected NIR light beam will be irradiated onto front optical window 11. The 2W output power of the VCSEL heats up front optical window 11 to prevent fogging of the front optical window. It will be appreciated that front optical window 11 may be any one of the NIR light-absorbing optical window described and illustrated in FIG. 4A to 4C. For example, front optical window 11 can be a NIR light-absorbing optical window including a sapphire substrate, a sapphire substrate with a glass plate that allows transmission of reflected visible light and/or fluorescence emission from a target area) while absorbing infrared and near infrared light having a NIR spectrum longer than 900 nm, a sapphire substrate doped with Yb and Er, and a sapphire substrate with an NIR-absorption coating.

It will be appreciated that the working principle of the second exemplary embodiment described in reference to FIG. 5 can also be applied to other embodiments such as embodiments described and illustrated in FIGS. 1A and 1B. In such embodiments, optical coupling module 2 is disposed between elongated member 1 including optical system 12 and coaxial coupling module 4. Optical system 12 and optical adapter module 2 have an imaging wavelength in the range from about 400 nm to about 900 nm. The optical components of optical system 12 and optical adapter module are coated with an antireflection coating in the wavelength range of 400 nm to 945 nm. In some embodiments, elongated member 1 can be the one described and illustrated in FIG. 3, and optical system 12 can be any one of the NIR light-absorbing optical window described and illustrated in FIG. 4A to 4C.

Figure 7:
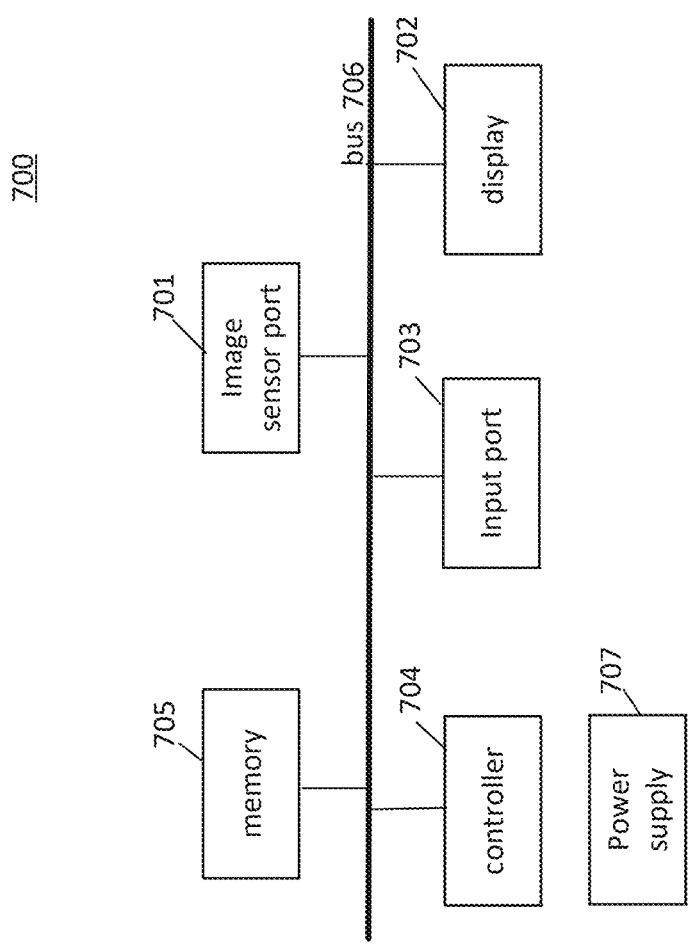
FIG. 7 is a simplified block diagram of a control system for an anti-fog device according to an embodiment of the present disclosure.

FIG. 7 is a simplified block diagram of a control system 700 for an anti-fog device according to an embodiment of the present disclosure. Control system 700 may include a plurality of control boxes, each control box may include an image sensor port 701 for receiving electrical signals from an image sensor, a display device 702 for displaying images corresponding to the received electrical signals, an input port 703 for receiving inputs and instructions from a user, a controller 704 for providing control signals to the different light sources (e.g., first light source 41, second light source 6 of FIG. 1B), and a memory device 705 configured to store data and instructions executed by controller 704. Image sensor port 701, display device 702, input port 703, controller 704, and memory device 705 are coupled to each other through a communication bus 706. Control system 700 may also include a power supply module 707 configured to provide power to the optical imaging system including the first and second semiconductor light sources, and the image sensor. Control system 700 may include additional components, such as a mouse, a keyboard, and other features, such as on-screen display menu, touch input, etc.

Figure 8:
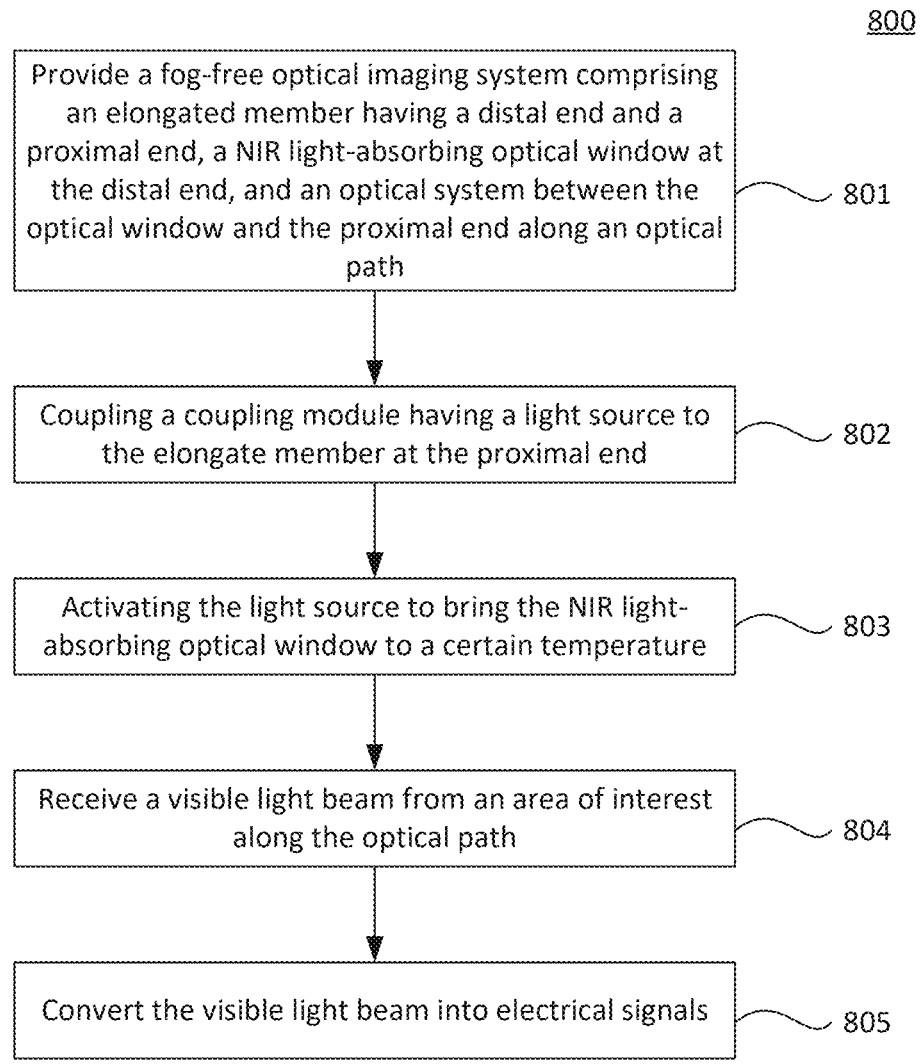
FIG. 8 is a simplified flowchart illustrating a method of operating a fog-free optical imaging system according to an embodiment of the present disclosure.

FIG. 8 is a simplified flowchart illustrating a method 800 of operating a fog-free optical imaging system according to an embodiment of the present disclosure. As an example, the devices depicted in FIGS. 1A, 1B, 5, and 6 can utilize the process illustrated in FIG. 8 for defogging the front optical window. Method 800 includes providing a fog-free optical imaging system having an elongated member comprising a distal end and a proximal end, a near-infrared (NIR) light-absorbing optical window disposed at the distal end, and an optical system disposed between the NIR light-absorbing optical window and the proximal end along an optical path (801). For example, the fog-free optical imaging system may be the optical imaging system 60 of FIG. 6. Method 800 also includes coupling a coupling module to the elongated member at the proximal end (802). The coupling module may include a dichroic mirror, a collimator, and a light source emitting NIR light. The NIR light can be transmitted to the NIR light-absorbing optical window along the optical path. Method 800 also includes activating the light source to transmit the NIR light to the NIR light-absorbing optical window along the optical path for an illumination time period (803), receiving a visible light beam reflected from an area of interest at an image sensor disposed along the along the optical path (804), and converting the visible light beam into electrical signals using the image sensor (805). The image sensor may include, for example, a CCD or a CMOS image sensor.

In some embodiments, method 800 further includes converting the electrical signals into frame data, and comparing the frame data between two frames to determine the illumination time period of the light source by a controller, and deactivating, by the controller, the light source after the illumination time period has expired. The frames that are compared may be consecutive frames.

In other embodiments, method 800 includes converting the electrical signals into image frames, determining, by a user or an operator, image quality of one or more of the image frames, and deactivating the light source, by the user or operator, when the user (operator) determines that image quality is satisfactory. In one embodiment, the image quality may be based on user observation and subjective judgment. In one embodiment, the image quality may be based on comparison of the obtained image against a set of predetermined images stored in a database or library. In one embodiment, the image quality may be based on artificial intelligence for image recognition.

In one embodiment, method 800 may also include adjusting a focal length of the fog-free optical imaging system using an optical adapter disposed between the elongated member and the image sensor. In one embodiment, method 800 may also include attenuating a portion of a reflected NIR light by an NIR light blocking filter disposed between the coupling module and the image sensor.

It should be appreciated that the specific steps illustrated in FIG. 8 provide a particular method of operating a fog-free optical imaging system according to an embodiment of the present disclosure. In some embodiments, the light source in the coupling module is activated prior to the insertion of the fog-free optical imaging system into a moist medium. In other embodiments, the light source in the coupling module is activated after the fog-free optical imaging system has been inserted into a moist medium. In yet other embodiments, the light source is only activated for a predetermined illumination time period. In other embodiments, a user or an operator may deactivate the light source when the NIR light-absorbing optical window has reached a predetermined temperature, e.g., 36.2 degrees Celsius of a human body, or other body temperatures of mammals. One of ordinary skill in the art would recognize many variations, modifications, and alternatives.

Figure 9A:
FIG. 9A is an image of a medium provided by a viewing device prior to activating an NIR light source according to an embodiment of the present disclosure.

FIG. 9A is an image of a moist medium provided by a viewing device prior to activating an NIR light source according to an embodiment of the present disclosure. In the image shown in FIG. 9A, the NIR light-absorbing optical window is fogged up on either the inside, outside or both, so that reflected visible light from an area of interest does not pass through the foggy NIR light-absorbing optical window, and the intensity of the captured visible light by an image sensor is weak, so that the displayed image in an image display device is blurry.

Figure 9B:
FIG. 9B is an image of the medium provided by the viewing device after the NIR light source has been activated according to an embodiment of the present disclosure.

FIG. 9B is an image of the medium provided by the viewing device after the NIR light has been activated according to an embodiment of the present disclosure. As shown in FIG. 9B, the NIR light-absorbing optical window has been defogged after being illuminated by the light source for a certain time period. As a result, the reflected displayed image visible light from the area of interest passes through the defogged NIR light-absorbing optical window, and the image display device shows a clear image.

According to embodiments of the present disclosure, an anti-fog device for a visible light only endoscope imaging system and an anti-fog device for a visible light and NIR (ICG) light endoscope imaging system are provided. In one exemplary embodiment of an anti-fog device for a visible light only endoscope imaging system, first semiconductor light source 41 can have an infrared laser device having a wavelength spectrum longer than 700 nm, e.g., around 808 nm. The optical components of optical system 12 and/or optical adapter module 2 may have an anti-reflective coating covering the range of 400 nm to 850 nm. In one exemplary embodiment of an anti-fog device for a visible light and NIR (ICG) light endoscope imaging system, the excitation wavelength of an IR laser device in second semiconductor source 6 may be around 780 nm and 800 nm, e.g., around 780 nm-785 nm. A LED device having a wavelength range of 780 nm and 805 nm may also be used.

In one embodiment, the excitation wavelength is centered at 789 nm and the emission wavelength is centered around 814 nm with a bandwidth of about 40 nm. NIR light blocking filter 5 is configured to block both the excitation wavelength 780 nm to 800 nm and the NIR wavelength 935 nm and 945 nm and pass wavelengths of visible light (400-700 nm) and fluorescence emission light (whose wavelengths are longer than those of the excitation light). For example, if the excitation wavelengths are in the range of 780-800 nm, e.g., 789 nm, the fluorescence emission light are in the range of 790-830 nm, e.g., 814 nm. In one embodiment, NIR light block filter 5 may include an ICG blocking filter for blocking excitation wavelength 780-800 nm and an anti-fog blocking filter for blocking NIR wavelength 935-945 nm. The ICG blocking filter and the anti-fog blocking filter are connected in series. In one embodiment, NIR light block filter 5 may include a single multi-notch filter having at least a first attenuating region configured to attenuate excitation wavelengths in the range 780-800 nm and a second attenuating region configured to attenuate NIR wavelengths in the range 935-945 nm.

In one embodiment, second semiconductor light source 6 may include a white light source, a UV light, and an NIR laser or NIR LED. In one embodiment, the UV light has a wavelength centered at about 415 nm.

While embodiments have been described in detail, it should be understood that various changes, substitutions, and modifications can be made hereto without departing from the scope of the present disclosure as defined by the appended claims.

What is claimed is:

1. A device for maintaining an optical path of an optical imaging system free of fog, the device comprising:
    an elongated member disposed along an optical axis and comprising:
        a distal end and a proximal end;
        an interface section disposed between the distal end and the proximal end;
        a near-infrared (NIR) light-absorbing optical window disposed at the distal end; and
        an optical system disposed along the optical axis, wherein the optical system comprises at least one optical lens element positioned along the optical axis; and
    a light source coupled to the interface section, wherein the light source is configured to transmit light toward an area of interest through a plurality of optical fibers disposed circumferentially around the elongated member; and
    a coupling module coupled to the elongated member at the proximal end, wherein the coupling module includes a NIR light source operable to provide NIR light and is configured to:
        transmit the NIR light to the NIR light-absorbing optical window through the proximal end and the at least one optical lens element positioned along the optical axis; and
        receive a light beam from the area of interest along the optical axis.

2. The device of claim 1, wherein the NIR light-absorbing optical window comprises a sapphire glass having a glass plate attached to an inside surface of the sapphire glass facing the optical system, the glass plate being configured to transmit visible light while absorbing the NIR light, or a sapphire glass comprising a heat absorption coating facing the optical system.

3. The device of claim 1, wherein the NIR light-absorbing optical window comprises a sapphire glass doped with impurities operable to pass visible light and absorb the NIR light.

4. The device of claim 1, wherein the coupling module comprises:
    a dichroic mirror having a first surface, a second surface, a third surface facing toward the proximal end of the elongated member, and a fourth surface facing toward an image sensor; and
    a collimator in front of the first surface of the dichroic mirror along a first optical axis;
    wherein the NIR light source is disposed in a focal plane of the collimator along the first optical axis and configured to provide the NIR light, and
    wherein the second surface is configured to reflect the NIR light and pass through the light beam.

5. The device of claim 4, wherein the NIR light source comprises a laser diode (LD) or a vertical cavity surface emitting laser (VCSEL) having an output optical power equal to or greater than 1 Watt.

6. The device of claim 1, wherein the light beam comprises a spectral range between 400 nm and 700 nm or wherein the area of interest is configured to be excited by a NIR excitation light wavelength and produce a NIR emission light wavelength longer than the NIR excitation light wavelength.

7. The device of claim 1, further comprising:
    an image sensor; and
    an NIR light blocking filter disposed in front of the image sensor and configured to pass through the light beam and block the NIR light.

8. The device of claim 7, wherein the NIR light blocking filter comprises a first blocking filter configured to block excitation wavelengths and a second blocking filter configured to block the NIR light.

9. The device of claim 1, wherein the NIR light-absorbing optical window has an absorption rate of about 80% in a wavelength range between 805 nm and 810 nm or 935 nm and 945 nm.

10. The device of claim 1, further comprising:
    an optical adapter disposed between the elongated member and an image sensor, wherein the optical adapter includes a plurality of optical lens elements.

11. The device of claim 1, further comprising:
    a controller coupled to the coupling module and configured to control an illumination time period of the NIR light source in the coupling module for maintaining the optical path of the optical imaging system free of fog.

12. The device of claim 11, wherein the controller is configured to determine the illumination time period by comparing image clarity from frame to frame.

13. The device of claim 1, wherein the elongated member is configured to receive an endoscope.

14. The device of claim 1, further comprising a second light source emitting visible light, near-infrared (NIR) light, and ultra-violet (UV) light.

15. The device of claim 1, wherein the plurality of optical fibers are disposed along an inner surface of elongated member.

16. The device of claim 1, further comprising an image sensor disposed adjacent the proximal end, wherein the coupling module is disposed between the proximal end and the image sensor.

17. The device of claim 16, further comprising a NIR light blocking filter.

18. The device of claim 17, further comprising an optical module including optical lens elements, wherein the elongated member, the optical module, the coupling module, the NIR light blocking filter, and the image sensor are arranged sequentially and in order along the optical axis.

19. The device of claim 1, wherein the light source comprises a visible light source.

20. The device of claim 1, wherein the light source comprises an infrared (IR) light source.

* * * * *